(12) United States Patent
Thomson et al.

(10) Patent No.: US 11,382,686 B2
(45) Date of Patent: Jul. 12, 2022

(54) SURGICAL FORCEPS

(71) Applicant: COVIDIEN LP, Mansfield, MA (US)

(72) Inventors: Reid T. Thomson, Erie, CO (US);
Grant T. Sims, Boulder, CO (US);
Jeffrey R. Townsend, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1077 days.

(21) Appl. No.: 15/995,411

(22) Filed: Jun. 1, 2018

(65) Prior Publication Data

US 2018/0271588 A1 Sep. 27, 2018

Related U.S. Application Data

(63) Continuation of application No. 14/805,759, filed on Jul. 22, 2015, now Pat. No. 9,987,078.

(51) Int. Cl.
*A61B 18/12* (2006.01)
*A61B 18/14* (2006.01)
(Continued)

(52) U.S. Cl.
CPC ........ *A61B 18/1445* (2013.01); *A61B 17/282* (2013.01); *A61B 17/2816* (2013.01);
(Continued)

(58) Field of Classification Search
CPC ............ A61B 18/1442; A61B 18/1445; A61B 2018/00601; A61B 2018/00922;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| EP | 0591990 A2 | 4/1994 |
| WO | 2015017991 A1 | 2/2015 |

OTHER PUBLICATIONS

Partial European search report issued in corresponding application No. 16180493.5 dated Dec. 7, 2016.
(Continued)

*Primary Examiner* — Daniel W Fowler
(74) *Attorney, Agent, or Firm* — Carter, DeLuca & Farrell LLP

(57) ABSTRACT

A forceps includes a pair of shaft members, a pair of jaw members each including a distal body and a proximal flange, and a pair of electrode plates. The proximal flanges are engaged with the respective shaft members and pivotably coupled to each other such that pivoting the shaft members pivots the distal jaw bodies. The electrode plates each includes a tissue-contacting portion disposed on the distal body of the respective jaw member and a proximal extension portion extending at least partially through the proximal flange of the respective jaw member. The tissue-contacting portion and proximal extension portion of the first electrode plate are disposed in perpendicular planes relative to each other. Likewise, the tissue-contacting portion and proximal extension portion of the second electrode plate are disposed in perpendicular planes relative to each other.

14 Claims, 7 Drawing Sheets

(51) Int. Cl.
*A61B 18/08* (2006.01)
*A61B 17/28* (2006.01)
*A61B 17/3201* (2006.01)
*A61B 18/00* (2006.01)

(52) U.S. Cl.
CPC ........ *A61B 17/3201* (2013.01); *A61B 18/085* (2013.01); *A61B 18/1442* (2013.01); *A61B 2018/00601* (2013.01); *A61B 2018/00922* (2013.01); *A61B 2018/1452* (2013.01); *A61B 2018/1457* (2013.01); *A61B 2018/1465* (2013.01)

(58) Field of Classification Search
CPC .... A61B 2018/1452; A61B 2018/1457; A61B 2018/1465
See application file for complete search history.

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,813,902 | A | 7/1931 | Bovie |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Willis |
| 2,279,753 | A | 4/1942 | Knopp |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |
| 3,651,811 | A | 3/1972 | Hildebrandt et al. |
| 3,720,896 | A | 3/1973 | Beierlein |
| 3,862,630 | A | 1/1975 | Balamuth |
| 3,863,339 | A | 2/1975 | Reaney et al. |
| 3,866,610 | A | 2/1975 | Kletschka |
| 3,911,766 | A | 10/1975 | Fridolph et al. |
| 3,913,586 | A | 10/1975 | Baumgarten |
| 3,920,021 | A | 11/1975 | Hiltebrandt |
| 3,921,641 | A | 11/1975 | Hulka |
| 3,938,527 | A | 2/1976 | Rioux et al. |
| 3,952,749 | A | 4/1976 | Fridolph et al. |
| 3,970,088 | A | 7/1976 | Morrison |
| 3,987,795 | A | 10/1976 | Morrison |
| 4,005,714 | A | 2/1977 | Hiltebrandt |
| 4,041,952 | A * | 8/1977 | Morrison, Jr. ......... A61B 17/30 606/42 |
| 4,043,342 | A | 8/1977 | Morrison, Jr. |
| 4,074,718 | A | 2/1978 | Morrison, Jr. |
| 4,088,134 | A | 5/1978 | Mazzariello |
| 4,112,950 | A | 9/1978 | Pike |
| 4,127,222 | A | 11/1978 | Adams |
| 4,128,099 | A | 12/1978 | Bauer |
| 4,165,746 | A | 8/1979 | Burgin |
| 4,233,734 | A | 11/1980 | Bies |
| 4,300,564 | A | 11/1981 | Furihata |
| D263,020 | S | 2/1982 | Rau, III |
| 4,370,980 | A | 2/1983 | Lottick |
| 4,375,218 | A | 3/1983 | DiGeronimo |
| 4,416,276 | A | 11/1983 | Newton et al. |
| 4,418,692 | A | 12/1983 | Guay |
| 4,452,246 | A | 6/1984 | Bader et al. |
| 4,492,231 | A | 1/1985 | Auth |
| 4,552,143 | A | 11/1985 | Lottick |
| 4,574,804 | A | 3/1986 | Kurwa |
| 4,597,379 | A | 7/1986 | Kihn et al. |
| 4,600,007 | A | 7/1986 | Lahodny et al. |
| 4,655,215 | A | 4/1987 | Pike |
| 4,655,216 | A | 4/1987 | Tischer |
| 4,657,016 | A | 4/1987 | Garito et al. |
| 4,662,372 | A | 5/1987 | Sharkany et al. |
| 4,671,274 | A | 6/1987 | Sorochenko |
| 4,685,459 | A | 8/1987 | Koch et al. |
| 4,715,122 | A | 12/1987 | Linden |
| D295,893 | S | 5/1988 | Sharkany et al. |
| D295,894 | S | 5/1988 | Sharkany et al. |
| 4,754,892 | A | 7/1988 | Retief |
| 4,763,669 | A | 8/1988 | Jaeger |
| 4,827,929 | A | 5/1989 | Hodge |
| 4,846,171 | A | 7/1989 | Kauphusman et al. |
| 4,887,612 | A | 12/1989 | Esser et al. |
| 4,938,761 | A | 7/1990 | Ensslin |
| 4,985,030 | A | 1/1991 | Melzer et al. |
| 5,007,908 | A | 4/1991 | Rydell |
| 5,026,370 | A | 6/1991 | Lottick |
| 5,035,695 | A | 7/1991 | Weber, Jr. et al. |
| 5,084,057 | A | 1/1992 | Green et al. |
| 5,099,840 | A | 3/1992 | Goble et al. |
| 5,116,332 | A | 5/1992 | Lottick |
| 5,147,357 | A | 9/1992 | Rose et al. |
| 5,151,102 | A | 9/1992 | Kamiyama et al. |
| 5,176,695 | A | 1/1993 | Dulebohn |
| 5,190,541 | A | 3/1993 | Abele et al. |
| 5,196,009 | A | 3/1993 | Kirwan, Jr. |
| 5,197,964 | A | 3/1993 | Parins |
| 5,215,101 | A | 6/1993 | Jacobs et al. |
| 5,217,457 | A | 6/1993 | Delahuerga et al. |
| 5,217,458 | A | 6/1993 | Parins |
| 5,217,460 | A | 6/1993 | Knoepfler |
| 5,219,354 | A | 6/1993 | Choudhury et al. |
| 5,244,462 | A | 9/1993 | Delahuerga et al. |
| 5,250,047 | A | 10/1993 | Rydell |
| 5,250,063 | A | 10/1993 | Abidin et al. |
| 5,258,001 | A | 11/1993 | Corman |
| 5,258,006 | A | 11/1993 | Rydell et al. |
| 5,261,918 | A | 11/1993 | Phillips et al. |
| 5,275,615 | A | 1/1994 | Rose |
| 5,277,201 | A | 1/1994 | Stern |
| 5,282,799 | A | 2/1994 | Rydell |
| 5,290,286 | A | 3/1994 | Parins |
| 5,304,203 | A | 4/1994 | El-Mallawany et al. |
| 5,308,357 | A | 5/1994 | Lichtman |
| 5,314,445 | A | 5/1994 | Heidmueller nee Degwitz et al. |
| 5,318,589 | A | 6/1994 | Lichtman |
| 5,324,289 | A | 6/1994 | Eggers |
| 5,326,806 | A | 7/1994 | Yokoshima et al. |
| 5,330,471 | A | 7/1994 | Eggers |
| 5,334,183 | A | 8/1994 | Wuchinich |
| 5,334,215 | A | 8/1994 | Chen |
| 5,336,220 | A | 8/1994 | Ryan et al. |
| 5,336,221 | A | 8/1994 | Anderson |
| 5,342,359 | A | 8/1994 | Rydell |
| 5,342,381 | A | 8/1994 | Tidemand |
| 5,342,393 | A | 8/1994 | Stack |
| 5,344,424 | A | 9/1994 | Roberts et al. |
| 5,352,222 | A | 10/1994 | Rydell |
| 5,354,271 | A | 10/1994 | Voda |
| 5,356,408 | A | 10/1994 | Rydell |
| 5,366,477 | A | 11/1994 | LeMarie, III et al. |
| 5,368,600 | A | 11/1994 | Failla et al. |
| 5,376,089 | A | 12/1994 | Smith |
| 5,383,897 | A | 1/1995 | Wholey |
| 5,389,098 | A | 2/1995 | Tsuruta et al. |
| 5,389,104 | A | 2/1995 | Hahnen et al. |
| 5,391,166 | A | 2/1995 | Eggers |
| 5,391,183 | A | 2/1995 | Janzen et al. |
| 5,396,900 | A | 3/1995 | Slater et al. |
| 5,403,312 | A | 4/1995 | Yates et al. |
| 5,411,519 | A | 5/1995 | Tovey et al. |
| 5,411,520 | A | 5/1995 | Nash et al. |
| 5,413,571 | A | 5/1995 | Katsaros et al. |
| 5,415,657 | A | 5/1995 | Taymor-Luria |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,292 | A | 8/1995 | Kipshidze et al. |

(56) References Cited

U.S. PATENT DOCUMENTS

| | | |
|---|---|---|
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,140 A | 10/1995 | Linden et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,591,202 A | 1/1997 | Slater et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,083 A | 10/1998 | Shemesh et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,976,132 A * | 11/1999 | Morris ............... A61B 18/1445 128/DIG. 22 |
| 5,984,939 A | 11/1999 | Yoon |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka |
| 6,024,741 A | 2/2000 | Williamson, IV et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |

(56) References Cited

U.S. PATENT DOCUMENTS

| | | |
|---|---|---|
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,060,695 A | 5/2000 | Harle et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,312,430 B1 | 11/2001 | Wilson et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,503,248 B1 | 1/2003 | Levine |
| 6,506,189 B1 | 1/2003 | Rittman, III et al. |
| 6,511,480 B1 | 1/2003 | Tetzlaff et al. |
| 6,514,251 B1 | 2/2003 | Ni et al. |
| 6,514,252 B2 | 2/2003 | Nezhat et al. |
| 6,527,771 B1 | 3/2003 | Weadock et al. |
| 6,544,264 B2 | 4/2003 | Levine et al. |
| 6,558,385 B1 | 5/2003 | McClurken et al. |
| 6,562,037 B2 | 5/2003 | Paton et al. |
| 6,569,162 B2 | 5/2003 | He |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |

(56) References Cited

U.S. PATENT DOCUMENTS

| | | |
|---|---|---|
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0193153 A1 | 9/2004 | Sartor et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0137590 A1 | 6/2005 | Lawes et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |

(56) References Cited

U.S. PATENT DOCUMENTS

| | | |
|---|---|---|
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0215048 A1 | 9/2008 | Hafner et al. |
| 2012/0172873 A1 | 7/2012 | Artale et al. |
| 2013/0018411 A1 | 1/2013 | Collings et al. |
| 2015/0112338 A1 | 4/2015 | Unger et al. |

OTHER PUBLICATIONS

Extended European Search Report issued in corresponding application No. 16180493.5 dated Feb. 16, 2017.

* cited by examiner

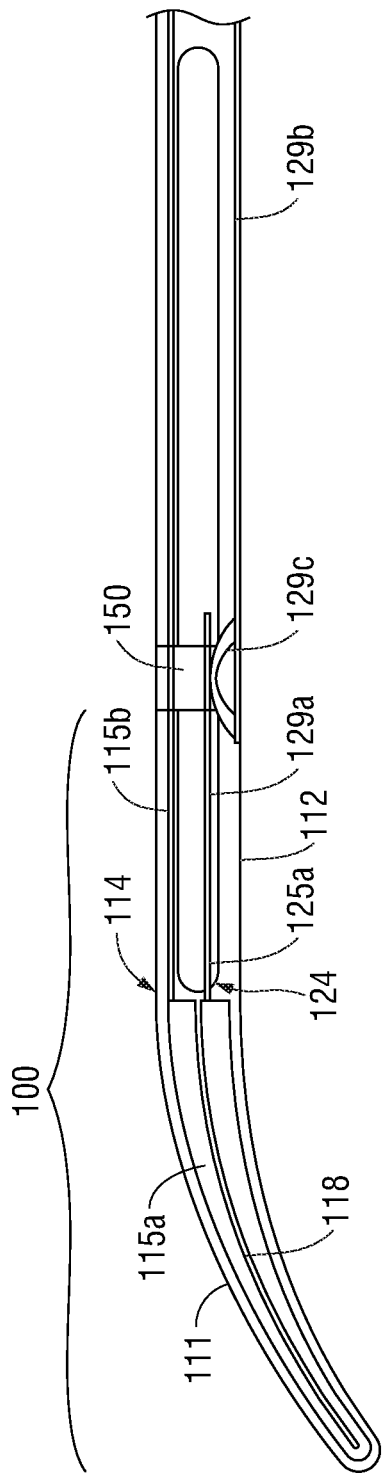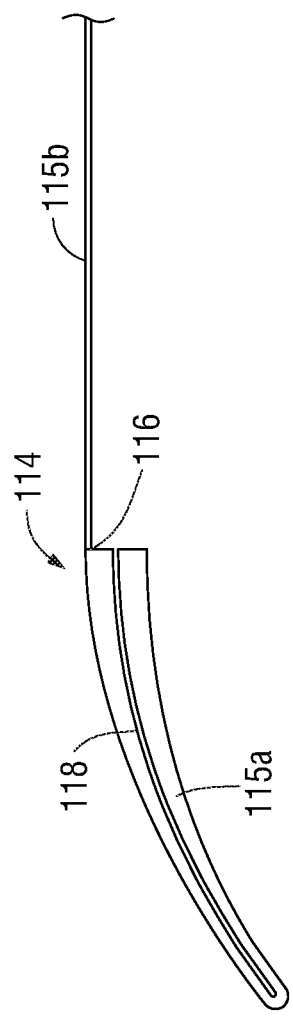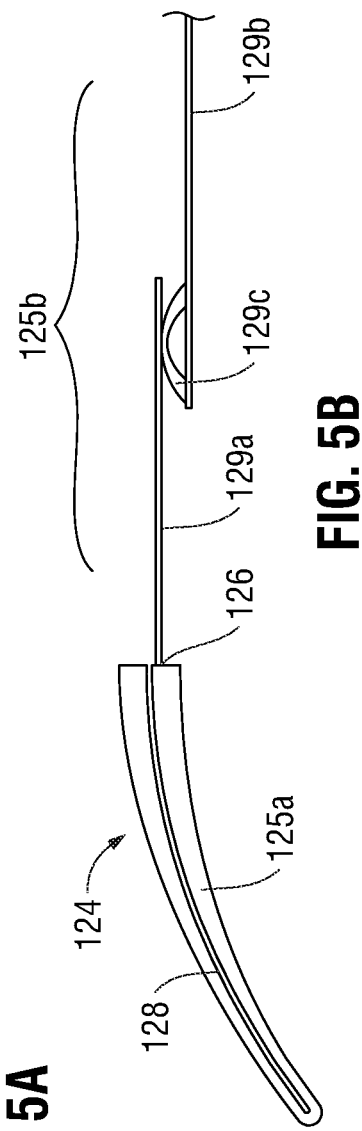

SURGICAL FORCEPS

CROSS-REFERENCE TO RELATED APPLICATIONS

This application is a continuation application of U.S. patent application Ser. No. 14/805,759, filed on Jul. 22, 2015, the entire contents of which are hereby incorporated herein by reference.

BACKGROUND

Technical Field

The present disclosure relates to surgical forceps and, more particularly, to an open surgical forceps for grasping, treating, and/or dividing tissue.

Background of Related Art

A forceps is a plier-like instrument which relies on mechanical action between its jaws to grasp, clamp, and constrict tissue. Electrosurgical forceps utilize both mechanical clamping action and electrical energy to treat tissue, e.g., by heating tissue to coagulate, cauterize, and/or seal tissue.

Typically, once tissue is treated, the surgeon has to accurately sever the tissue along the treated portion thereof. Accordingly, many forceps have been designed to incorporate a knife which is deployable to effectively sever tissue after treatment thereof.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with aspects of the present disclosure, a forceps is provided including first and second shaft members, first and second jaw members, and first and second electrode plates. The first and second shaft members each define a proximal end and a distal end. The first and second jaw members each include a distal jaw body and a proximal flange. The proximal flanges of the first and second jaw members are engaged with the respective first and second shaft members and are pivotably coupled to each other such that pivoting the first and second shaft members relative to each other from an open position to a closed position pivots the distal jaw bodies of the first and second jaw members relative to each other from a spaced-apart position to an approximated position. The first electrode plate is coupled to the first jaw member and includes a tissue-contacting portion disposed on the distal jaw body of the first jaw member and a proximal extension portion extending proximally from the tissue-contacting portion at least partially through the proximal flange of the first jaw member. The tissue-contacting portion and the proximal extension portion are disposed in perpendicular planes relative to each other. The second electrode plate is coupled to the second jaw member and includes a tissue-contacting portion disposed on the distal jaw body of the second jaw member and a proximal extension portion extending proximally from the tissue-contacting portion at least partially through the proximal flange of the second jaw member. The tissue-contacting portion and the proximal extension portion are disposed in perpendicular planes relative to each other.

In an aspect of the present disclosure, the proximal extension portion of the first electrode plate extends through the proximal flange of the first jaw member and at least partially through the first shaft member. Additionally or alternatively, the proximal extension portion of the first electrode plate extends about the pivot.

In another aspect of the present disclosure, the proximal extension portion of the second electrode plate includes a first segment and a second segment. The first segment extends at least partially through the proximal flange of the second jaw member and is substantially disposed distally of the pivot. The second segment extends at least partially through the proximal flange of the first jaw member and is substantially disposed proximally of the pivot. The second segment extends at least partially through the first shaft member. A spring washer disposed about the pivot may be provided for electrically coupling the first and second segments of the proximal extension portion of the second electrode plate with each other.

In yet another aspect of the present disclosure, an activation button disposed on the first shaft member or the second shaft member is provided. In such aspects, the proximal extension portion of at least one of the first or second electrode plates is electrically coupled to the activation button.

In still another aspect of the present disclosure, an electrosurgical cable extends from the first shaft member or the second shaft member. In such aspects, the proximal extension portion of at least one of the first or second electrode plates is electrically coupled to the electrosurgical cable.

In still yet another aspect of the present disclosure, the first and second shaft members are biased towards the open position thereby biasing the first and second jaw members towards the spaced-apart position.

In another aspect of the present disclosure, a knife assembly is operably coupled to one of the first shaft member or the second shaft member and includes a knife blade disposed within one of the first jaw member or the second jaw member. In such aspects, the first and second shaft members are movable from the closed position to a cutting position to move the knife blade from a retracted position to an extended position, wherein the knife blade extends at least partially between the first and second jaw members.

In another aspect of the present disclosure, at least one of the tissue-contacting portion of the first electrode plate or the tissue-contacting portion of the second electrode plate defines a knife channel configured to permit passage of the knife blade therethrough.

Another forceps provided in accordance with the present disclosure includes first and second shaft members each defining a proximal end and a distal end, first and second jaw members, a knife assembly, an activation button, and an activation assembly. The first and second jaw members are engaged with the respective first and second shaft members and coupled to each other such that moving the first and second shaft members relative to each other from an open position to a closed position moves the first and second jaw members relative to each other from a spaced-apart position to an approximated position. The knife assembly is operably coupled to one of the first shaft member or the second shaft member and includes a knife blade disposed within one of the first jaw member or the second jaw member. The first and second shaft members are movable from the closed position to a cutting position to move the knife blade from a retracted position to an extended position, wherein the knife blade extends at least partially between the first and second jaw members. The activation button is disposed on the first shaft member and configured for selective activation to supply energy to the first and second jaw members. The activation assembly is disposed within the second shaft member and positioned to oppose the activation button. The activation assembly includes a foot movably disposed within a cavity defined within the second shaft member. As such, moving the first and second shaft members relative to each other from the open position to the closed position urges the foot into contact with the activation button to supply energy to the first and second jaw members. Further, moving the first and second shaft members relative to each other from the closed position to the cutting position urges the activation button into contact with the foot such that the foot is recessed into the cavity and at least a portion of the activation button is accommodated within the cavity.

In an aspect of the present disclosure, the first and second shaft members are movable relative to each other from the closed position to the cutting position independent of movement of the first and second jaw members. In such aspects, one of the first or second shaft members may be coupled to the respective first or second jaw member via a flexible connection permitting movement of the first and second shaft members relative to each other from the closed position to the cutting position independent of movement of the first and second jaw members.

In another aspect of the present disclosure, the knife assembly includes a knife bar engaged with of the first shaft member or the second shaft member. The knife bar is coupled to the knife blade such that movement of the first and second shaft members from the closed position to the cutting position moves the knife blade relative to the first and second jaw members from the retracted position to the extended position.

In still another aspect of the present disclosure, the first and second shaft members are biased towards the open position thereby biasing the first and second jaw members towards the spaced-apart position.

In yet another aspect of the present disclosure, the foot is coupled to the second shaft member via a biasing member that biases the foot outwardly from the cavity.

In still yet another aspect of the present disclosure, the biasing member defines a biasing force that is greater than a force required to activate the activation button.

In another aspect of the present disclosure, a first electrode plate is coupled to the first jaw member. The first electrode plate includes a tissue-contacting portion disposed on the first jaw member and a proximal extension portion extending proximally from the tissue-contacting portion at least partially through the first shaft member.

In another aspect of the present disclosure, a second electrode plate is coupled to the second jaw member. The second electrode plate includes a tissue-contacting portion disposed on the second jaw member and a proximal extension portion extending proximally from the tissue-contacting portion at least partially through the first shaft member.

In yet another aspect of the present disclosure, the proximal extension portion of the second electrode plate includes a first segment and a second segment. The first segment extends at least partially through the second jaw member and the second segment extending at least partially through the first jaw member and at least partially through the first shaft member.

BRIEF DESCRIPTION OF THE DRAWINGS

Various aspects and features of the present disclosure are described herein with reference to the drawings wherein:

FIG. 4 is a top, cross-sectional view of the distal end of the forceps of FIG. 1;

FIG. 5A is a top view of the electrode of one of the jaw members of the forceps of FIG. 1;

FIG. 5B is a top view of the electrode of the other jaw member of the forceps of FIG. 1;

DETAILED DESCRIPTION

Figure 1:
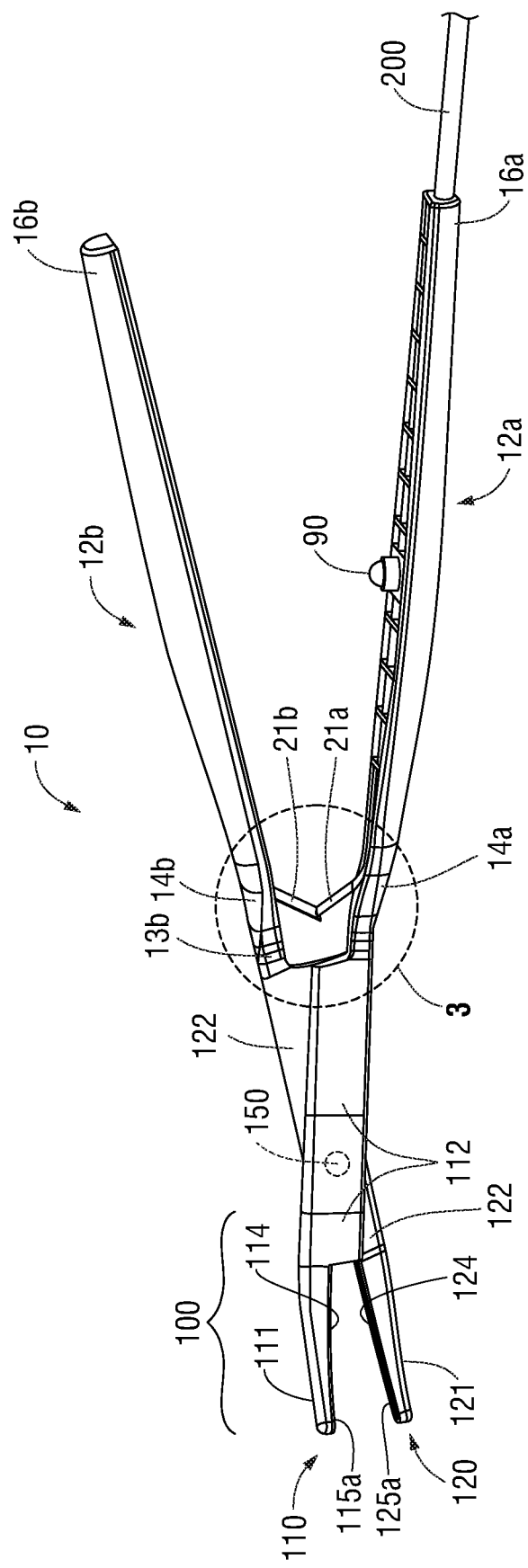
FIG. 1 is a side, perspective view of a forceps provided in accordance with the present disclosure.

Referring to FIG. 1, a forceps 10 provided in accordance with the present disclosure is shown including first and second shaft members 12a, 12b each having a distal end 14a, 14b and a proximal end 16a, 16b, respectively. An end effector assembly 100 is disposed at the distal ends 14a, 14b of shaft members 12a, 12b. End effector assembly 100 includes first and second jaw members 110, 120, each including a distal jaw body 111, 121 and a proximal flange 112, 122 coupled to a respective one of the first and second shaft members 12a, 12b. The respective distal jaw bodies 111, 121 and proximal flanges 112, 122 of jaw members 110, 120 may be integrally formed with one another and shaft members 12a, 12b, respectively, e.g., via molding, and are formed from an electrically-insulative material, e.g., plastic. One of the shaft members, e.g., shaft member 12b, is coupled to its respective proximal flange 122 via a flexible connection 13b, e.g., a living hinge, the importance of which is detailed below.

A pivot pin 150 pivotably couples proximal flanges 112, 122 of jaw members 110, 120 with one another. Thus, with pivot pin 150 extending through proximal flanges 112, 122 and being disposed between the respective shaft members 12a, 12b and the respective jaw members 110, 120, shaft members 12a, 12b may be moved relative to one another about pivot pin 150 between an open position (FIG. 1) and an activated or closed position (FIGS. 7A and 7B) to effect movement of jaw members 110, 120 relative to one another about pivot pin 150 between a spaced-apart position (FIG. 1) and an approximated position (FIG. 7B), respectively, for grasping tissue therebetween. As detailed below, shaft members 12a, 12b are further movable towards one another, independent of movement of jaw members 110, 120, from the activated or closed position (FIG. 7A) to a cutting position (FIG. 8A) via flexion of flexible connection 13b for cutting treated tissue grasped between jaw members 110, 120.

Figure 3:
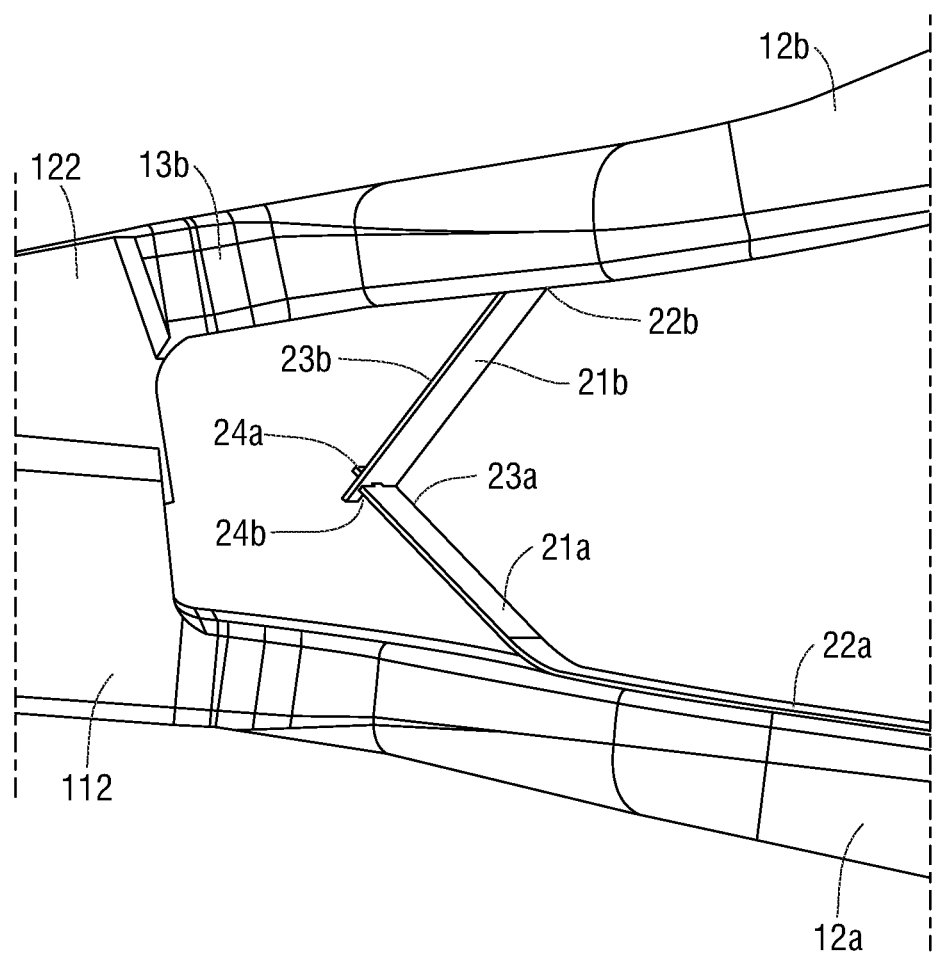
FIG. 3 is an enlarged, side, perspective view of the area of detail indicated as "3" in FIG. 1.

With momentary reference to FIG. 3, each shaft member 12a, 12b includes a flat spring 21a, 21b, or other suitable biasing member, engaged thereto at a first end 22a, 22b of the respective flat spring 21a, 21b. Second ends 23a, 23b of flat springs 21a, 21b define complementary engagement features, e.g., a tab 24a and slot 24b, so as to enable engagement of second ends 23a, 23b of flat springs 21a, 21b with one another. As a result of this configuration and with flat springs 21a, 21b biased to resist flexion, shaft members 12a, 12b are biased apart from one another towards the open position (FIG. 1), thereby biasing jaw members 110, 120 towards the spaced-apart position (FIG. 1).

Figure 2:
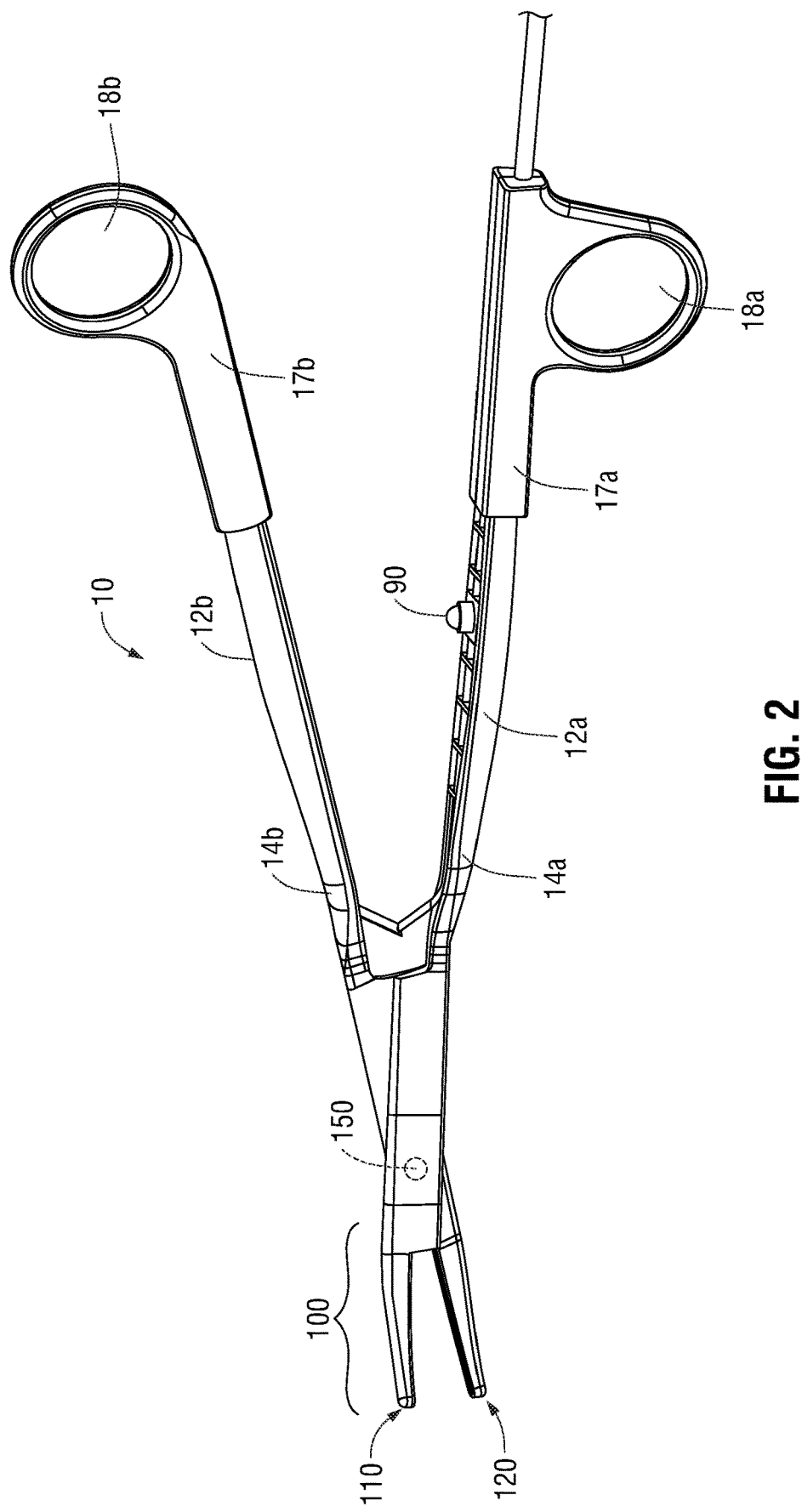
FIG. 2 is a side, perspective view of the forceps of FIG. 1 including handles disposed thereon.

Referring briefly to FIG. 2, each shaft member 12a, 12b may include a handle 17a, 17b releasably engagable with the proximal end 16a, 16b thereof. Each handle 17a, 17b defines a finger hole 18a, 18b therethrough for receiving a finger of the user. As can be appreciated, finger holes 18a and 18b facilitate movement of shaft members 12a and 12b relative to one another. Handles 17a, 17b may be formed from first and second components configured to releasably engage one another about shaft members 12a, 12b, e.g., in snap-fit engagement, may define lumens configured to receive the proximal ends 16a, 16b of shaft members 12a, 12b, respectively, or may be releasably or fixedly engaged with shaft members 12a, 12b in any other suitable fashion.

Returning to FIG. 1, one of the shaft members, e.g., shaft member 12a, is configured to operably couple with an electrosurgical cable 200 at the proximal end 16a of shaft member 12a. Electrosurgical cable 200 is configured to couple to a source of electrosurgical energy such as an electrosurgical generator (not shown). Electrosurgical cable 200 may be permanently secured to proximal end 16a of shaft member 12a or may be releasably engagable therewith. Electrosurgical cable 200 houses one or more wires (not shown) that extend therethrough. The wires (not shown) are configured to couple to electrode plates 114, 124 (FIG. 6) to supply electrosurgical energy to jaw members 110, 120. Shaft member 12a further includes an activation button 90 supported thereon and positioned to oppose shaft member 12b. Activation button 90 is electrically coupled with either or both of electrode plates 114, 124 (FIG. 6), as detailed below, to enable the selective supply of energy to jaw members 110, 120. The other shaft member, e.g., shaft member 12b, includes a knife assembly 80 (FIGS. 7A-8B) disposed therein and an actuation assembly 92 (FIGS. 7A and 8A) operably coupled thereto for enabling deployment of knife blade 84 of knife assembly 80 (see FIG. 8B) and the selective actuation of activation button 90, respectively, as will also be detailed below.

With reference to FIGS. 1 and 4-6, each jaw member 110, 120 of end effector assembly 100 includes an electrically-conductive electrode plate 114, 124 associated therewith. Electrode plates 114, 124 each include a tissue-contacting portion 115a, 115b disposed in a first plane, and a proximal extension portion 115b, 125b disposed in a second plane or multiple second planes disposed in perpendicular orientation relative to the first plane. Tissue-contacting portions 115a, 125a and proximal extension portions 115b, 125b of electrode plates 114, 124, respectively, are monolithically formed with one another, e.g., each electrode plate 114, 124 is formed from a single sheet of material. Thus, in order to achieve the perpendicular orientation of tissue-contacting portions 115a, 125a relative to respective proximal extension portions 115b, 125b, electrode plates 114, 124 define twisted sections 116, 126 interconnecting respective tissue-contacting portions 115a, 125a and respective proximal extension portions 115b, 125b. Either or both of tissue-contacting portions 115a, 125a of electrode plates 114, 124 may further define a longitudinally-extending knife channel 118, 128 defined therethrough.

Jaw members 110, 120 each include, as mentioned above, a distal jaw body 111, 121 and a proximal flange 112, 122. Tissue-contacting portions 115a, 125a of electrode plates 114, 124, respectively, are disposed on respective distal jaw bodies 111, 121 of jaw members 110, 120 in opposing relation relative to one another such that, upon movement of jaw members 110, 120 from the spaced-apart position to the approximated position, tissue can be grasped between tissue-contacting portions 115a, 125a of electrode plates 114, 124. As detailed below, with tissue grasped between tissue-contacting portions 115a, 125a of electrode plates 114, 124, electrode plates 114, 124 may be energized to conduct energy through tissue grasped therebetween to treat tissue.

Proximal extension portions 115b, 125b of electrode plates 114, 124 extend proximally from respective tissue-contacting portions 115a, 125a and distal jaw bodies 111, 121, and at least partially through proximal flanges 112, 122 of jaw members 110, 120, respectively. More specifically, proximal extension portion 115b of electrode plate 114 of jaw member 110 extends through proximal flange 112, about pivot pin 150, and proximally through shaft member 12a, ultimately coupling to activation button 90 and one or more of the wires (not shown) of electrosurgical cable 200 (see FIG. 6). To permit routing about pivot pin 150, proximal extension portion 115b of electrode plate 114 may include an aperture or slot (not shown) configured to receive pivot pin 150 therethrough, although other configurations are also contemplated.

Proximal extension portion 125b of electrode plate 124, which extends proximally from distal jaw body 121 into proximal flange 122 of jaw member 120 defines an interruption dividing proximal extension portion 125b into first and second segments 129a, 129b. First segment 129a of proximal extension portion 125b is substantially disposed distally of pivot pin 150 (although a small portion, e.g., less than 10% of its length, extends proximally beyond pivot pin 150), while second segment 129b of proximal extension portions 125b is substantially disposed proximally of pivot pin 150 (although a small portion, e.g., less than 10% of its length, extends distally beyond pivot pin 150).

Figure 6:
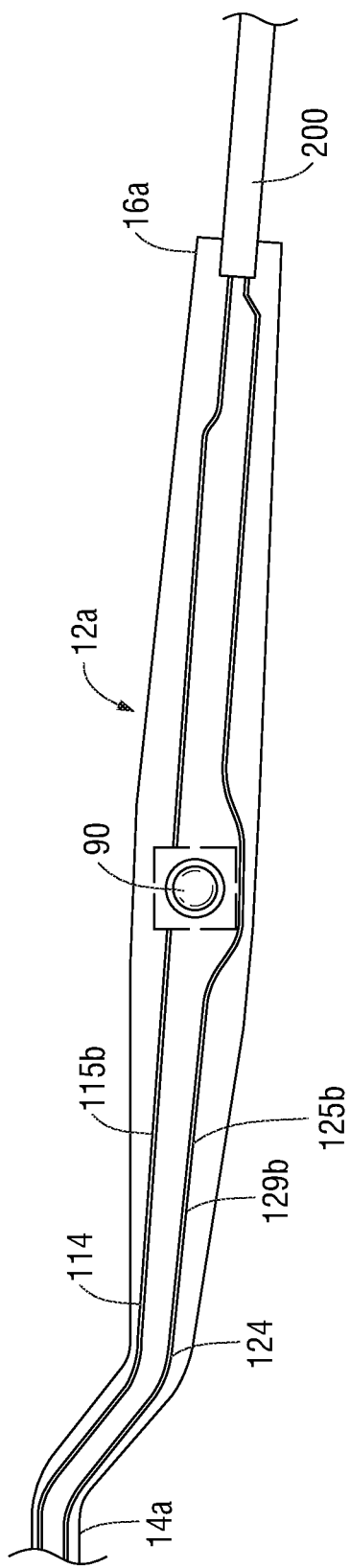
FIG. 6 is a top view of one of the shaft members of the forceps of FIG. 1 with a portion thereof removed to illustrate the internal components thereof.

The above-noted interrupted configuration of proximal extension portion 125b of electrode plate 124 allows first segment 129a of proximal extension portion 125b to extend through proximal flange 122 of jaw member 120, while second segment 129b of proximal extension portion 125b extends through proximal flange 112 of jaw member 110, and proximally through shaft member 12a, ultimately coupling to activation button 90 and one or more of the wires (not shown) of electrosurgical cable 200 (see FIG. 6). A spring washer 129c disposed about pivot pin 150 is provided for maintaining electrical communication between first and second segments 129a, 129b of proximal extension portion 125b of electrode plate 124 regardless of the positioning of shaft members 12a, 12b relative to one another about pivot pin 150. First and second segments 129a, 129b, respectively, may define slots or apertures (not shown) to permit passage about pivot pin 150, similarly as detailed above with respect to electrode plate 114, although other configurations are also contemplated.

Referring in particular to FIG. 6, as detailed above, proximal extension portion 115b of electrode plate 114 and second segment 129b of proximal extension portion 125b of electrode plate 124 extend through shaft member 12a, ultimately coupling to activation button 90 and one or more of the wires (not shown) of electrosurgical cable 200. Further, with shaft member 12a (as well as shaft member 12b (FIG. 1)) formed from an electrically-insulative material, a user is protected from contacting electrode plates 114, 124 while grasping shaft member 12a.

Turning now to FIGS. 1 and 7A-8B, shaft member 12b, as noted above, includes a knife assembly 80. Knife assembly 80 includes a knife bar 82 and a knife blade 84. Knife bar 82 is fixedly engaged within shaft member 12b at the proximal end of knife bar 82 and extends distally through shaft member 12b and proximal flange portion 122 (FIG. 1) of jaw member 120. Knife bar 82 defines an aperture 83 configured to receive pivot pin 150 to permit passage of knife bar 82 about pivot pin 150 and enable pivoting of knife bar 82 relative to pivot pin 150. Knife blade 84 extends distally from knife bar 82 and, in a retracted position thereof, is housed within distal jaw body 121 of jaw member 120 (FIG. 7B). Knife blade 84 defines a sharpened upper cutting surface 85 and is pivotable about pivot pin 150 and relative to jaw members 110, 120 from the retracted position (FIG. 7B) to an extended position (FIG. 8B), wherein knife blade 84 extends at least partially from knife channel 128 (FIG. 5B) of jaw member 120 between tissue-contacting portions 115a, 125a of electrode plates 114, 124 to cut tissue grasped therebetween. In the extended position, knife blade 84 may further extend at least partially through knife channel 118 (FIG. 5A) of jaw member 110, in embodiments where such a channel is provided.

Figure 7A:
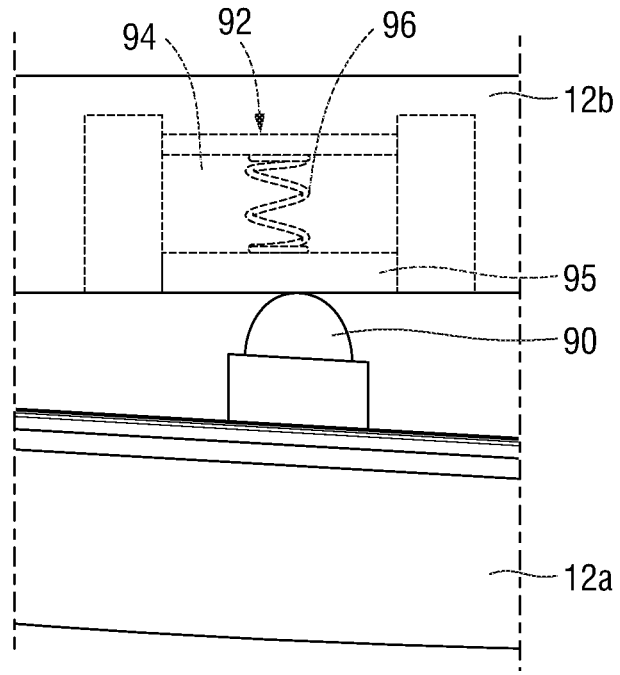
FIG. 7A is a side view of a portion of the actuation assembly and shaft members of the forceps of FIG. 1, disposed in an activated or closed position.
Figure 7B:
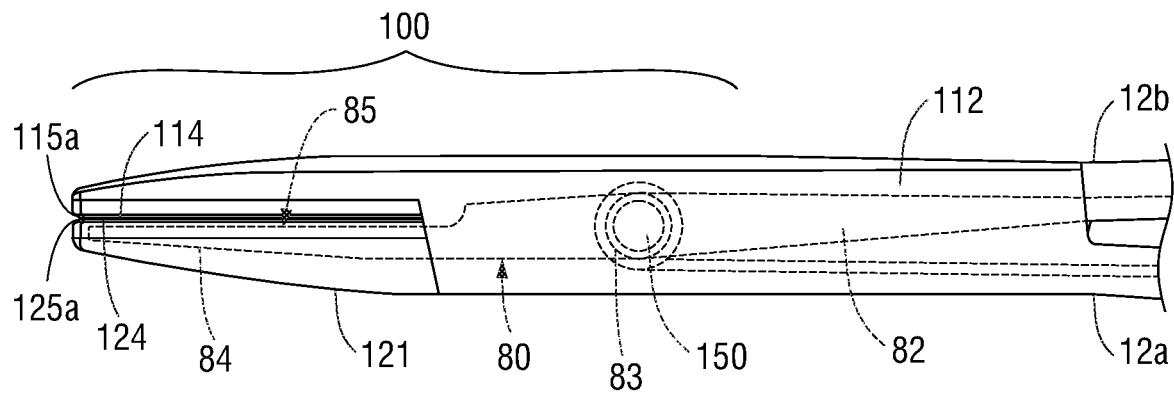
FIG. 7B is a side view of the distal end of the forceps of FIG. 1, disposed in the activated or closed position.
Figure 8A:
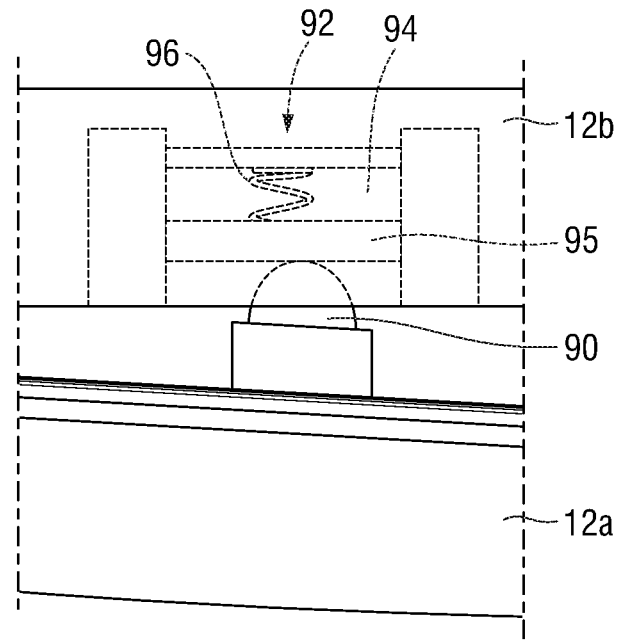
FIG. 8A is a side view of a portion of the actuation assembly and shaft members of the forceps of FIG. 1, disposed in a cutting position.
Figure 8B:
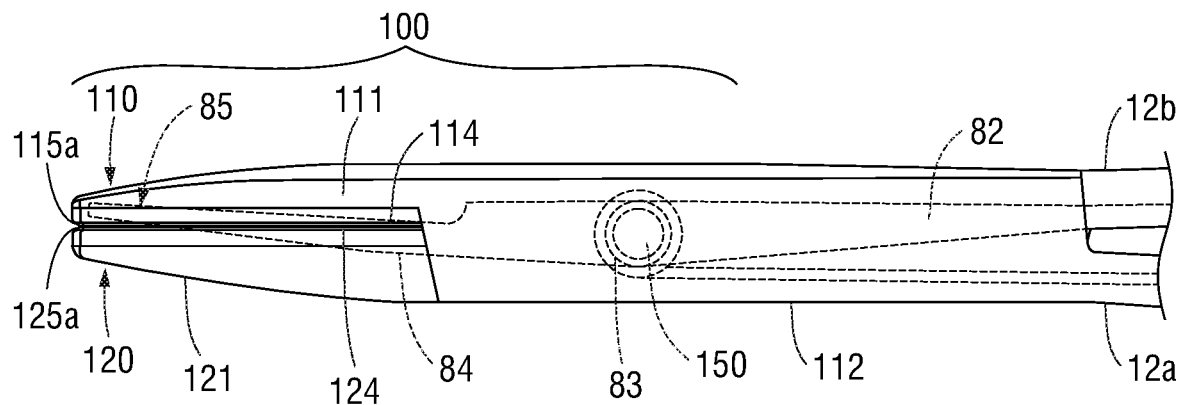
FIG. 8B is a side view of the distal end of the forceps of FIG. 1, disposed in the cutting position.

Knife blade 84 is moved from the retracted position (FIG. 7B) to the extended position (FIG. 8B) in response to movement of shaft members 12a, 12b, independent of movement of jaw members 110, 120, from the activated or closed position (FIG. 7A) to a cutting position (FIG. 8A). Such movement of shaft members 12a, 12b is enabled via flexion of flexible connection 13b, which permits flexion of shaft member 12b relative to jaw member 120. More specifically, with knife bar 82 fixedly engaged within shaft member 12b, as shaft member 12 is flexed relative to jaw member 120 via flexion of flexible connection 13b, knife bar 82 and, thus, knife blade 84 are likewise moved relative to jaw member 120. Upon sufficient flexion of shaft member 12b relative to jaw member 120, knife blade 84 is moved from the retracted position (FIG. 7B) to the extended position (FIG. 8B). Flexible connection 13b is biased so as to normally align shaft member 12b with jaw member 120 in generally linear longitudinal alignment, thus biasing knife blade 84 towards the retracted position (FIG. 7B).

With continued reference to FIGS. 7A-8B, as also noted above, shaft member 12b includes an actuation assembly 92 operably coupled thereto for enabling the selective actuation of activation button 90. Actuation assembly 92 is further configured to accommodates activation button 90 upon deployment of knife blade 84 of knife assembly 80, thus inhibiting damage to activation button 90 when shaft members 12a, 12b are moved to the cutting position. More specifically, actuation assembly 92 is disposed within a cavity 94 defined within shaft member 12b and is positioned to oppose activation button 90 of shaft member 12a. Actuation assembly 92 includes a foot 95 disposed within cavity 94. Foot 95 is coupled to shaft member 12b via a biasing member 96, e.g., a coil spring, biased such that foot 95 is substantially flush with the surface of shaft member 12b, although other configurations are also contemplated.

With particular reference to FIGS. 7A and 7B, biasing member 96 defines a biasing force that is greater than the force required to activate activation button 90 such that, upon movement of shaft members 12a, 12b from the open position to the activated or closed position to move jaw members 110, 120 to the approximated position for grasping tissue therebetween, foot 95 is urged into contact with activation button 90 and activates activation button 90 while being maintained in substantially flush position relative to the surface of shaft member 12b. In the activated or closed position of activation button 90, the supply of energy to tissue-contacting portions 115a, 125a of electrode plates 114, 124 of jaw members 110, 120 is initiated. More specifically, tissue-contacting portions 115a, 125a of electrode plates 114, 124 of jaw members 110, 120 are energized to different potentials such that an electrical potential gradient is created therebetween, allowing for the conduction of energy through tissue grasped between jaw members 110, 120 to treat tissue.

With particular reference to FIGS. 8A and 8B, the biasing force of biasing member 96 is less than the force required to flex flexible connection 13b such that, upon further urging of shaft members 12a, 12b from the activated or closed position to the cutting position, foot 95 is recessed into cavity 94 via the activation button 90 and against the bias of biasing member 96, thus permitting movement of shaft member 12a, 12b to the cutting position while cavity 94 accommodates activation button 90 therein. As detailed above, upon movement of shaft members 12a, 12b to the cutting position, knife blade 84 of knife assembly 180 is moved to the extended position, wherein knife blade 84 extends at least partially through knife channel 128 of jaw member 120 (and, in some embodiments, into knife channel 118 of jaw member 110) to cut tissue grasped between jaw members 110, 120.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of a surgical instrument, comprising:
   first and second jaw members, the first jaw member including a first distal jaw body and a first proximal flange extending proximally from the first distal jaw body, the second jaw member including a second distal jaw body and a second proximal flange extending proximally from the second distal jaw body, the first and second proximal flanges of the first and second jaw members pivotably coupled with one another to enable pivoting of the distal jaw bodies of the first and second jaw members relative to one another between a spaced-apart position and an approximated position;
   a first electrode plate coupled to the first jaw member, the first electrode plate including a first tissue-contacting portion disposed on the first distal jaw body and a first proximal extension portion extending proximally from the first tissue-contacting portion at least partially through the first proximal flange, the first tissue-contacting portion and the first proximal extension portion disposed in perpendicular orientation relative to one another; and
   a second electrode plate coupled to the second jaw member, the second electrode plate including a second tissue-contacting portion disposed on the second distal jaw body and a second proximal extension portion extending proximally from the second tissue-contacting portion at least partially through the second proximal flange, the second tissue-contacting portion and the second proximal extension portion disposed in perpendicular orientation relative to one another, wherein the first and second proximal flanges are pivotably coupled to one another about a pivot pin and wherein the second proximal extension portion includes a first segment and a second segment, the first segment extending at least partially through the second proximal flange and substantially disposed distally of the pivot pin, the second segment extending at least partially through the first proximal flange and substantially disposed proximally of the pivot pin.

2. The end effector assembly according to claim 1, wherein the first proximal extension portion extends about the pivot pin.

3. The end effector assembly according to claim 1, further including a spring washer disposed about the pivot pin and electrically coupling the first and second segments of the second proximal extension portion with one another.

4. The end effector assembly according to claim 1, wherein the distal jaw bodies of the first and second jaw members are biased towards the spaced-apart position.

5. The end effector assembly according to claim 1, wherein at least one of the first or second tissue-contacting portions defines a knife channel configured to permit passage of a knife blade therethrough.

6. A surgical instrument, comprising:
   first and second shaft members each defining a proximal end and a distal end;
   first and second jaw members, the first jaw member including a first proximal flange attached to the first shaft member and a first distal jaw body extending distally from the first proximal flange, the second jaw member including a second proximal flange attached to the second shaft member and a second distal jaw body extending distally from the second proximal flange, the first and second proximal flanges of the first and second jaw members pivotably coupled with one another about a pivot pin such that pivoting of the first and second shaft members relative to one another from an open position to a closed position pivots the first and second distal jaw bodies relative to one another from a spaced-apart position to an approximated position;
   a first electrode plate coupled to the first jaw member, the first electrode plate including a first tissue-contacting portion disposed on the first distal jaw body and a first proximal extension portion extending proximally from the first tissue-contacting portion at least partially through the first proximal flange, the first tissue-contacting portion and the first proximal extension portion disposed in perpendicular orientation relative to one another; and
   a second electrode plate coupled to the second jaw member, the second electrode plate including a second tissue-contacting portion disposed on the second distal jaw body and a second proximal extension portion extending proximally from the second tissue-contacting portion at least partially through the second proximal flange, the second tissue-contacting portion and the second proximal extension portion disposed in perpendicular orientation relative to one another, wherein the second proximal extension portion includes a first segment and a second segment, the first segment extending at least partially through the second proximal flange and substantially disposed distally of the pivot pin, the second segment extending at least partially through the first proximal flange, substantially disposed proximally of the pivot pin, and extending at least partially through the first shaft member.

7. The surgical instrument according to claim 6, wherein the first proximal extension portion extends through the first proximal flange and at least partially through the first shaft member.

8. The surgical instrument according to claim 7, wherein the first proximal extension portion extends about the pivot pin.

9. The surgical instrument according to claim 6, further including a spring washer disposed about the pivot pin and electrically coupling the first and second segments of the second proximal extension portion with one another.

10. The surgical instrument according to claim 6, further including an activation button disposed on the first shaft member or the second shaft member, wherein at least one of the first or second proximal extension portions is electrically coupled to the activation button.

11. The surgical instrument according to claim 6, further including an electrosurgical cable extending from the first shaft member or the second shaft member, wherein at least one of the first or second proximal extension portions is electrically coupled to the electrosurgical cable.

12. The surgical instrument according to claim 6, wherein the first and second shaft members are biased towards the open position thereby biasing the first and second jaw members towards the spaced-apart position.

13. The surgical instrument according to claim 6, further including a knife assembly operably coupled to one of the first shaft member or the second shaft member and including a knife blade disposed within one of the first jaw member or the second jaw member, the first and second shaft members movable from the closed position to a cutting position to move the knife blade from a retracted position to an extended position, wherein the knife blade extends at least partially between the first and second jaw members.

14. The surgical instrument according to claim 13, wherein at least one of the first or second tissue-contacting portions defines a knife channel configured to permit passage of the knife blade therethrough.

* * * * *